(12) United States Patent
Zhao et al.

(10) Patent No.: US 7,652,769 B2
(45) Date of Patent: Jan. 26, 2010

(54) METHOD AND APPARATUS FOR ASSESSING PURITY OF VEGETABLE OILS BY MEANS OF TERAHERTZ TIME-DOMAIN SPECTROSCOPY

(75) Inventors: Ziran Zhao, Beijing (CN); Zhiqiang Chen, Beijing (CN); Yingxin Wang, Beijing (CN); Bing Feng, Beijing (CN); Li Zhang, Beijing (CN); Zhuoyan Liu, Beijing (CN); Yinpeng Liang, Beijing (CN)

(73) Assignees: Tsinghua University, Beijing (CN); Nuctech Company, Beijing (CN)

( * ) Notice: Subject to any disclaimer, the term of this patent is extended or adjusted under 35 U.S.C. 154(b) by 132 days.

(21) Appl. No.: 11/966,057

(22) Filed: Dec. 28, 2007

(65) Prior Publication Data

US 2008/0165364 A1     Jul. 10, 2008

(30) Foreign Application Priority Data

Dec. 31, 2006    (CN) .................... 2006 1 0171613

(51) Int. Cl.
G01B 9/02     (2006.01)
G01J 3/45     (2006.01)
(52) U.S. Cl. .................................... 356/451
(58) Field of Classification Search ................ 356/300, 356/301, 450, 451, 456
See application file for complete search history.

(56) References Cited

U.S. PATENT DOCUMENTS 6,556,306 B2 *  4/2003  Jiang et al. .................. 356/517
6,747,736 B2 *  6/2004  Takahashi .................... 356/319
7,023,545 B2 *  4/2006  Slater ........................ 356/326
2008/0084564 A1 * 4/2008  He et al. ..................... 356/456
2008/0149819 A1 * 6/2008  Zhdaneev .................... 250/255

OTHER PUBLICATIONS

"Rapid Quantitative Assessment of the Adulteration of Virgin Olive Oils with Hazelnut Oils using Raman Spectroscopy and Chemometrics" by E. Lopez-Diez et al., *American Chemical Society*, 2003, pp. 6145-6150.
"A New Adulteration Detection Method on Edible Vegetable Oils by gas Chromatography", by W. Ming et al., *China Academic Journal Electronic Publishing House*, vol. 24, No. 12, 2003, pp. 103-106.

* cited by examiner

*Primary Examiner*—Michael A Lyons
(74) *Attorney, Agent, or Firm*—Westman, Champlin & Kelly, P.A.

(57) ABSTRACT

The present invention relates to a method for assessing the purity of vegetable oils by means of THz time-domain spectroscopy, comprising the steps of: measuring the THz time-domain spectra of standard vegetable oils to establish a spectral database; measuring the THz time-domain spectrum of vegetable oil to be detected; analyzing the purity of the detected vegetable oil based on the pre-built database. The present invention also relates to an apparatus for assessing purity of vegetable oil by means of THz time-domain spectroscopy, comprising: spectrum measuring device for measuring time-domain waveforms of THz pulses before and after transmitting the vegetable oil held in a container by transmission approach, or directly measuring time-domain waveforms of THz pulses before and after reflecting from the vegetable oil by reflection approach; and data processing device for extracting physical parameters of the vegetable oil in THz region according to the time-domain waveforms. Compared with the prior art, the method according to the present invention is easy, rapid and quantitative.

10 Claims, 2 Drawing Sheets

METHOD AND APPARATUS FOR ASSESSING PURITY OF VEGETABLE OILS BY MEANS OF TERAHERTZ TIME-DOMAIN SPECTROSCOPY

BACKGROUND OF THE INVENTION

The present application claims priority of Chinese patent application Serial No. 200610171613.7, filed Dec. 31, 2006, the content of which is hereby incorporated by reference in its entirety.

1. Field of the Invention

The present invention relates to terahertz time-domain spectroscopy analysis, and more particularly, to a method and an apparatus for assessing the purity of vegetable oils by mean of terahertz (hereinafter referred as "THz" for short) time-domain spectroscopy.

2. Description of the Prior Art

Edible vegetable oils are necessary to people, but the prices thereof vary greatly dependent on the categories and nutritive values. In recent years, some illegal producers incorporate some low-cost vegetable oils into high-cost vegetable oils to enlist profits, and thus some categories of adulterated vegetable oils appear in the market. It is a problem to be solved in the quality supervision that how to assess the truth of the vegetable oils and analyze the category of the adulterated vegetable oils and the adulterated amount. Therefore, an easy, quick and reliable assessment is needed in order to protect legal producers and customers.

The conventional method to assess vegetable oils is mostly dependent on the physical chemistry characteristics such as solidifying point, refractive index, degree of unsaturation and iodine value, but it is only roughly qualitative detection method. Currently, the technology that can make quantitative assessment on adulterated vegetable oils mainly includes chromatographic analysis and spectroscopic analysis methods.

Document 1 (WEI Ming, etc., A New Adulteration Detection Method on Edible Vegetable Oils by Gas Chromatography, Food Science, 2003, 24(12), 103-106) discloses a method for assessing the vegetable oil adulteration by measuring composition and content of fatty acid in the vegetable oil through gas chromatography. Gas chromatography is a physical separation method, and the principle thereof is that different substances have different distribution coefficients in a system composed of two phases, i.e., stationary phase and mobile phase. When these two phases move relative to each other, these substances move along with the mobile phase, and distribute between these two phases repeatedly. Therefore it is possible to make the substances whose distribution coefficients have tiny difference have greatly different moving speeds, so that respective components are completely separated. Vegetable oils mainly are some categories of glyceride made of fatty acid such as palmitic acid, stearic acid, oleic acid, linoleic acid and the likes, and composition and content of the fatty acid of different categories of vegetable oil are different, thus the composition and content of fatty acid will change after adulteration. The purpose of discriminating the category of adulterated oil and computing the adulterated amount can be achieved by assessing composition of the fatty acid by means of gas chromatography, and comparing with that of a category of pure oil.

However, when gas chromatography is used to assess composition and content of fatty acid, it is necessary to methyl-esterify the fatty acid first. Currently, a vitriol-methanol or potassium hydroxide-methanol system is used to perform methyl-esterification under normal temperature or warmed condition. However, this procedure takes some time (generally 20~30 minutes), which does not meet the requirement of practical application for rapidly detecting batch of samples. Furthermore, this method is a destructive method, that is to say, this method changes the composition of the detected sample, and so the sample can not be reutilized.

Document 2 (E. C. López-Díez, et al. Rapid quantitative assessment of the adulteration of virgin olive oils with hazelnut oils using Raman spectroscopy and chemometrics. <Journal of Agricultural and Food Chemistry>, 2003, 51(21):6145-6150) discloses a rapid quantitative assessment of the adulteration of olive oils using Raman spectroscopy and chemometrics. Raman spectroscopy is a kind of molecular vibration spectroscopy, and the physical basis is Raman scattering effect induced by inelastic scattering of molecules to incident light. Position of Raman spectral line reflects the molecular structure characteristic and can be used in qualitative analysis because difference chemical bonds or radicals have different vibrations; intensity of Raman spectral line is in proportion to the intensity of incident light and concentration of sample molecules, and can be used as basis of qualitative analysis. Document 2 utilized a dispersive instrument employing a laser to measure Raman spectra of high quality virgin olive oils and refined hazelnut oils first, and discriminated these two vegetable oils whose chemical properties are very close by using the spectra data as eigenvectors. The model of the Raman spectra data of virgin olive oils adulterated with hazelnut oils in different concentrations was constructed through the Partial Least Squares algorithm, and the purity of the olive oils was predicted by the constructed model.

As stated above, Raman spectrum, which is considered as a fingerprint of a given oil, can reflect the structure characteristic of molecules, and can make rapid quantitative assessment of the adulteration of vegetable oils in combination with chemometrics. This method will not change the composition of the sample, and neither preliminary treatment of the sample nor complicated sample preparation procedure is needed. However, the disadvantage of Raman spectroscopy is in that the efficiency of Raman scattering is low and the scattered light is so weak as to be overwhelmed by the fluorescence generated by the sample or the impurity in the sample, whereby the detection accuracy will be affected.

THz technology is an advanced technology that is newly developed, which relates to generation, detection and application of THz radiation (commonly refers to electromagnetic waves with a frequency range of 0.1-10 THz. THz-TDS is one of the most important technologies of terahertz radiation applications, and the basic idea is to obtain absorption and dispersion spectrum of the sample in THz region by measuring the waveforms of THz pulses before and after transmitting the sample. Many organic molecules have strong absorption and dispersion in THz frequency range due to vibrational and rotational transition of dipoles. THz spectra of different substances often reveal specific features, and provide unique identification information fingerprint) for the molecule conformation, by means of which the substance components can be discriminated. Therefore, this technology can be widely used in various fields such as quality control and security inspection

SUMMARY OF THE INVENTION

An object of the present invention is to provide an easy, rapid and quantitative method for assessing the purity of vegetable oils by means of THz time-domain spectroscopy.

In order to achieve the object of the present invention, the present invention provides a method for assessing a purity of vegetable oils by means of THz time-domain spectroscopy, comprising the steps of:

1) measuring the THz time-domain spectra of standard vegetable oils to establish a spectral database;
2) measuring the THz time-domain spectrum of vegetable oil to be detected;
3) analyzing the purity of the detected vegetable oil based on the pre-built database.

Preferably, step 1) comprises using THz-TDS instrument to measure time-domain waveforms of THz pulses before and after transmitting the standard vegetable oil or reflecting from the standard vegetable oil, extracting the physical parameters of the standard vegetable oil in the THz waveband according to the time-domain waveforms, and establishing the THz spectrum of the standard vegetable oil based on the physical parameters.

Preferably, step 2) comprises using THz-TDS instrument to measure time-domain waveforms of THz pulses before and after transmitting the detected vegetable oil or reflecting from the detected vegetable oil, extracting the physical parameters of the detected vegetable oil in the THz waveband according to the time-domain waveforms, and establishing the THz spectrum of the detected vegetable oil based on the physical parameters.

The spectral database should include the data of the standard vegetable oil of different categories, different producers, different producing areas, different storage time, and different temperatures.

The standard vegetable oil is a sample of vegetable oil whose parameters such as composition and purity are known.

The physical parameters preferably comprises at lease one of absorption coefficient, refractive index and complex dielectric constant.

Preferably, step 3) comprises using a mathematical method of statistical analysis to quantitatively analyze the purity of the detected vegetable oil and content of each composition when the vegetable oil is adulterated.

Preferably, the statistical analysis method comprises a model-based method which establishes a regression model of THz spectrum of the standard vegetable oil and the purity of the vegetable oil by a regression analysis method, and assesses the purity of the detected vegetable oil based on the model.

Preferably, the statistical analysis method comprises a recognition-based method which simplifies the THz spectrum data structure by a pattern recognition method, and analyzes correlation of the spectra or similarity of sample points to discriminate the category of the vegetable oil.

Preferably, the pattern recognition method comprises a principal component analysis method or a clustering method.

Preferably, the statistical analysis method comprises a method which combines the model-based method and the recognition-based method, and can achieve regression modeling, spectral data structure simplification and correlation analysis of two groups of spectra.

Preferably, the statistical analysis method comprises a partial least squares regression method.

The present invention also provides an apparatus for assessing purity of vegetable oil by means of THz time-domain spectroscopy, comprising:

spectrum measuring device for measuring time-domain waveforms of THz pulses before and after transmitting the vegetable oil held in a container by transmission approach, or directly measuring time-domain waveforms of THz pulses before and after reflecting from the vegetable oil by reflection approach; and data processing device for extracting physical parameters of the vegetable oil in THz region according to the time-domain waveforms.

The spectrum measuring device comprises a scanning optical delay line based THz-TDS system having one single femtosecond laser, or an asynchronous optical sampling technique or phase sampling technique based THz-TDS system having two femtosecond lasers.

The container is used to hold a certain amount of vegetable oil to perform THz spectroscopy measurement, and the manufacturing materials should have high transmissivities to THz radiation, such as High density polyethylene (HDPE), Teflon and the likes.

Consideration of the size of the container mostly focuses on the thickness of the wall, which is perpendicular to the propagation direction of THz wave, and the spacing between two walls. On one hand, it should be thick enough to avoid multiple reflection effect. On the other hand, it should be thin enough to avoid excess attenuation of the THz waves. The spacing between two walls is fixed or adjustable.

The reflection approach is to directly measure the detected object without unpacking and sampling.

The present invention has the following advantages over prior art due to the above method and structure:

1. In the method according to the present invention, when the transmission approach is used, sampling is easy, and complicated sample preparation procedure is unnecessary; when the reflection approach is used, sampling is unnecessary, and nondestructive detection can be achieved.

2. The present invention uses rapid THz-TDS measurement apparatus, and so there are no mechanical scanning delay lines in the conventional THz-TDS system, and the precision and the speed of measurement can be improved.

3. When the method and apparatus of present invention is used to measure vegetable oil sample, both the absorption spectrum and the dispersion spectrum can be obtained, and thus the number of features (amount of information) available in the discrimination procedure increases greatly, which enhances the capability of the present invention for assessing the purity of vegetable oils.

BRIEF DESCRIPTION OF THE DRAWINGS

The above and/or other aspects of the present invention will become apparent and more readily appreciated from the following description of the exemplary embodiments, taken in conjunction with the accompanying drawings, in which.

Figure 1:
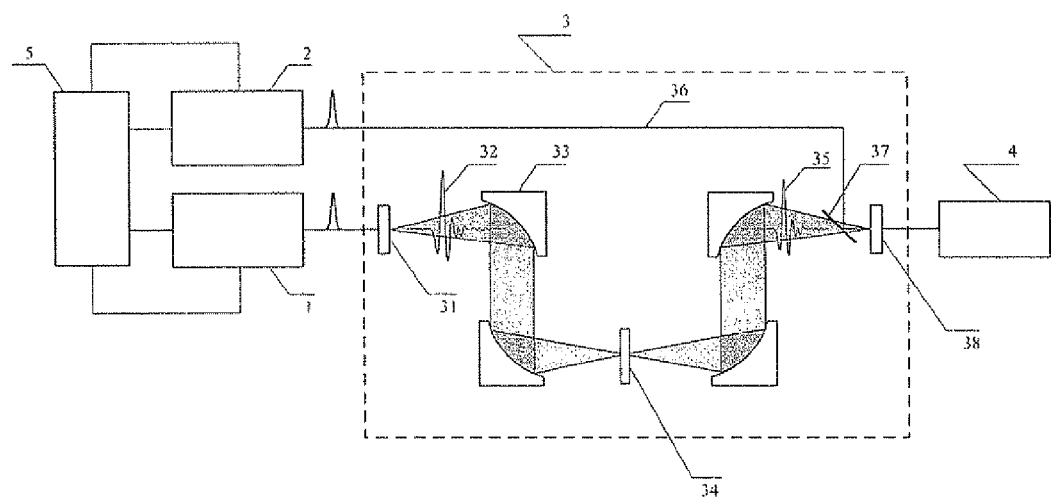
FIG. 1 shows a block diagram of an apparatus for assessing the purity of vegetable oils by means of THz spectroscopy.

DESCRIPTION OF REFERENCE NUMERALS 1 pump femtosecond laser generation device
2 probe femtosecond laser generation device
3 THz emission and detection components
4 data acquisition and processing system
5 femtosecond laser repetition frequency difference control device
31 THz emitter
32 THz waves
33 THz paraboloidal mirrors 34 sample
35 refocused THz waves
36 propagation path
37 probe laser reflector
38 THz detector

DETAILED DESCRIPTION OF THE PREFERRED EMBODIMENTS

Reference will now be made in detail to the embodiments of the present invention, examples of which are illustrated in the accompanying drawings, wherein like reference numerals refer to like elements throughout. The embodiments are described below to explain the present invention by referring to the figures.

FIG. 1 shows a block diagram of an apparatus for assessing the purity of vegetable oil by means of a THz-TDS system which is based on asynchronous optical sampling technique according to an embodiment of the present invention. As shown in FIG. 1, the apparatus according to an embodiment of the present invention comprises a pump femtosecond laser generation device 1; a probe femtosecond laser generation device 2; THz emission and detection component 3 which comprises a THz emitter 31, four paraboloidal mirrors 33; a sample stage for carrying a sample 34, a probe laser reflector 37, a THz detector 38; a data acquisition and processing system 4 and femtosecond laser repetition frequency difference control device 5.

The pump femtosecond laser beam and probe femtosecond laser beam are respectively generated by two femtosecond lasers with a difference operation frequency Δf, the delay between the pulses of the two beams is always changed. Let the repetition frequency of the pump beam be f, then in a time interval of Δf, the probe pulses scans the THz pulses in a time window of 1/f to obtain the time-domain waveform. The beam emitted from the femtosecond laser 1 is divided into two beams via a beam splitter, one beam acts as the pump beam and the other one is feedback to device 5 via a photoelectric detector; The beam emitted from the femtosecond laser in device 2 is also divided into two beams via a beam splitter, one beam acts as the probe beam and the other one is feedback to device 5 via a photoelectric detector. Device 5 controls the repetition frequency difference of the two femtosecond lasers to be hold at Δf according to these two feedback signals.

The data acquisition and processing system first converts the photoelectric signals outputted from the THz detector 38 into electric signals by a photoelectric converter, transmits them to the data acquisition unit, and then delivers the collected THz electric field intensity data to a computer to be processed, and displays in real time the time-domain waveforms of the THz pulses by means of a time-domain waveform collection program and a spectrum analysis program, and finally extracts the THz spectra of the detected sample.

As shown in FIG. 1, the femtosecond-pulse laser emitted from device 1 acts as a pump beam to excite the THz emitter 31 in component 3 to emit THz waves 32. The THz waves 32 interact with the sample 34 after they are focused by the paraboloidal mirrors 33, and then the refocused THz waves 35 arrive at the THz detector 38. The femtosecond-pulse laser emitted from device 2 acts as a probe beam, which travels along an optical path 36 and a reflector 37, and is incident on the detector 38 collinearly with the THz waves 35 to detect the instantaneous electric field intensity of the THz waves. After that, the detected signals are delivered to the data acquisition and processing system 4. The data acquisition and processing system 4 controls the entire apparatus to cooperate, and obtains electric field intensities of the THz pulses at different timings from the component 3, and finally gets time-domain waveforms of the THz pulses.

Figure 2:
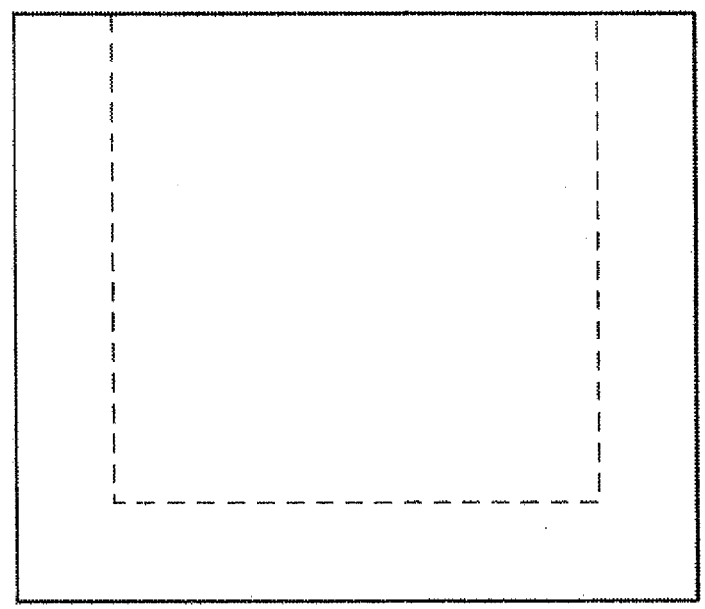
FIG. 2 shows a front view of the container.
Figure 3:
FIG. 3 shows a top view of the container.
Figure 4:
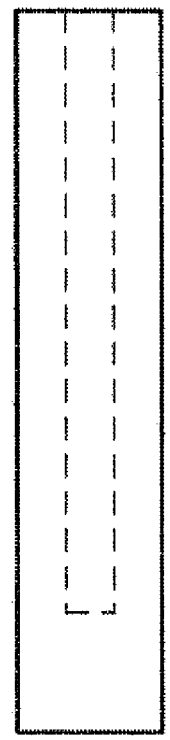
FIG. 4 shows a left view of the container.

FIG. 2 shows a front view of the vegetable oil container, FIG. 3 shows a top view of the container, and FIG. 4 shows a left view of the container. In FIG. 4, the vertical surface (perpendicular to the THz wave propagation direction) of the container should be as smooth as possible.

The extraction procedure of THz spectrum of vegetable oil is as following. As to the transmission-type THz-TDS system shown in FIG. 1, the THz pulse electric field measured when there is no vegetable oil in the container is defined as a reference signal $E_r(t)$, and the THz pulse electric field measured when there is vegetable oil in the container is defined as a sample signal $E_s(t)$. Assume that respective frequency components of the THz pulses are regarded as planar electromagnetic waves and incident on the detected sample vertically. According to Fresnel Equation, the refractive index and absorption coefficient of the vegetable oil are expressed as following:

$$n(\omega) = \frac{\phi(\omega)c}{\omega d} + 1 \quad (1)$$

$$\alpha(\omega) = \frac{2}{d}\ln\left(\frac{(n_0(\omega)+1)^2 n(\omega)}{\rho(\omega)(n(\omega)+n_0(\omega))^2}\right) \quad (2)$$

wherein c is the velocity of light in vacuum, ω is an angular velocity, d is a thickness of the vegetable oil to be detected, $n_0(\omega)$ is a refractive index of the container (which can be known in advance, because the material of the container has been known), $\rho(\omega)$ and $\phi(\omega)$ are amplitude ratio and phase difference between the sample and the reference signal, respectively, i.e., the amplitude and phase of transfer function $H(\omega)$ of the sample. The expression of $H(\omega)$ is as following:

$$H(\omega) = \frac{FT[E_s(t)]}{FT[E_r(t)]},$$

wherein FT represents Fourier Transform.

Equations (1) and (2) are approximation equations in the case that the sample is thick enough (above 1 mm) and the absorption is weak, and in the present invention, these two conditions can be reached. The complex dielectric constant can be derived according to the refractive index and the absorption coefficient. Therefore, the THz spectra of the vegetable oil, including the absorption spectrum $\alpha(\omega)$, the dispersion spectrum $n(\omega)$, and the dielectric spectrum, can be extracted by only assessing $E_r(t)$ and $E_s(t)$.

When the THz spectral database of the standard vegetable oil is to be established, it should be considered that the composition of the vegetable oil will vary as producing areas, producers, storage times and temperatures. Accordingly, vegetable oil samples of different categories, different producing areas, different producers, different storage times and different temperatures should be collected first, and then THz spectrum of each sample is assessed by the apparatus shown in FIG. 1 and then stored.

In the procedure of assessing the purity of the vegetable oil, there are two tasks to be solved. One is to discriminate whether the detected sample is adulterated and the category of the adulterated oil, and the other one is to determine the content of the adulterated oil (or the purity of the detected sample).

As to the first task, first, simplify the spectral data structure in the database of the standard vegetable oil by pattern recognition methods such as principal component analysis or cluster analysis, analyze the correlation of the spectra or similarity of the sample points (this step should be done only once after the spectral database of the standard vegetable oil has been established, and will not be performed during the assessment); secondly, do the same to the THz spectrum of the detected vegetable oil, and classify it according to a certain criterion. Whether the vegetable oil is adulterated can be determined based on the correlation of the vegetable oil with a known class or category of oil, and the category of the adulterated oil can be determined based on the correlation of the vegetable oil with other category of oil.

As to the second task, first, a regression model of the THz spectrum of the standard vegetable oil and the purity of the vegetable oil should be established by statistical analysis such as partial least squares regression; and then the purity of the detected vegetable oil is assessed by using this model.

Although the exemplary embodiments of the present invention have been shown and described, it will be appreciated by those skilled in the art that changes may be made in these embodiments without departing from the principles and spirit of the invention. The scope of which is defined in the appended claims and their equivalents.

What is claimed is:

1. A method for assessing a purity of vegetable oils by means of THz time-domain spectroscopy, comprising the steps of:
   a) measuring the THz time-domain spectra of standard vegetable oils to establish a spectral database;
   b) measuring the THz time-domain spectrum of vegetable oil to be detected; and
   c) analyzing the purity of the detected vegetable oil based on the pre-built database.

2. The method according to claim 1, wherein step a) comprises using THz-TDS instrument to measure time-domain waveforms of THz pulses before and after transmitting the standard vegetable oil or reflecting from the standard vegetable oil, extracting the physical parameters of the standard vegetable oil in the THz waveband according to the time-domain waveforms, and establishing the THz spectrum of the standard vegetable oil based on the physical parameters.

3. The method according to claim 1, wherein step b) comprises using THz-TDS instrument to measure time-domain waveforms of THz pulses before and after transmitting the detected vegetable oil or reflecting from the detected vegetable oil, extracting the physical parameters of the detected vegetable oil in the THz waveband according to the time-domain waveforms, and establishing the THz spectrum of the detected vegetable oil based on the physical parameters.

4. The method according to claim 2, wherein the physical parameters preferably comprises at least one of absorption coefficient, refractive index and complex dielectric constant.

5. The method according to claim 1, wherein step c) comprises using a mathematical method of statistical analysis to quantitatively analyze the purity of the detected vegetable oil and content of each composition when the vegetable oil is adulterated.

6. The method according to claim 5, wherein the statistical analysis method comprises a model-based method which establishes a regression model of THz spectrum of the standard vegetable oil and the purity of the vegetable oil by a regression analysis method, and assesses the purity of the detected vegetable oil based on the model.

7. The method according to claim 5, wherein the statistical analysis method comprises a recognition-based method which simplifies the THz spectrum data structure by a pattern recognition method, and analyzes correlation of the spectra or similarity of sample points to discriminate the category of the vegetable oil.

8. The method according to claim 7, wherein the pattern recognition method comprises a principal component analysis method or a clustering method.

9. The method according to claim 5, wherein the statistical analysis method comprises a method which combines the model-based method and the recognition-based method, and can achieve regression modeling, spectral data structure simplification and correlation analysis of two groups of spectra.

10. The method according to claim 9, wherein the statistical analysis method comprises a partial least squares regression method.

* * * * *